(12) United States Patent
Kumar et al.

(10) Patent No.: US 9,920,319 B2
(45) Date of Patent: Mar. 20, 2018

(54) 2'/3'/5'-(R/S)-SERINYL FUNCTIONALIZED OLIGONUCLEOTIDES

(71) Applicant: Council of Scientific & Industrial Research, New Delhi (IN)

(72) Inventors: Vaijayanti Anil Kumar, Maharashtra (IN); Venubabu Kotikam, Maharashtra (IN); Souvik Maiti, New Delhi (IN); Smita Nahar, New Delhi (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/888,794

(22) PCT Filed: May 2, 2014

(86) PCT No.: PCT/IN2014/000293
§ 371 (c)(1),
(2) Date: Nov. 3, 2015

(87) PCT Pub. No.: WO2014/178082
PCT Pub. Date: Nov. 6, 2014

(65) Prior Publication Data
US 2017/0044527 A1 Feb. 16, 2017

(30) Foreign Application Priority Data
May 3, 2013 (IN) .......................... 1308/DEL/2013

(51) Int. Cl.
| | | |
|---|---|---|
| C07H 21/02 | (2006.01) |
| C07H 21/04 | (2006.01) |
| C12N 15/113 | (2010.01) |
| C07H 19/067 | (2006.01) |
| C07H 19/10 | (2006.01) |
| C07H 21/00 | (2006.01) |

(52) U.S. Cl.
CPC ......... *C12N 15/113* (2013.01); *C07H 19/067* (2013.01); *C07H 19/10* (2013.01); *C07H 21/02* (2013.01); *C07H 21/00* (2013.01); *C12N 2310/113* (2013.01); *C12N 2310/321* (2013.01)

(58) Field of Classification Search
None
See application file for complete search history.

(56) References Cited

FOREIGN PATENT DOCUMENTS

| | | |
|---|---|---|
| EP | 0626387 A1 | 11/1994 |
| WO | 2012149906 A1 | 11/2012 |

OTHER PUBLICATIONS

Igloi Analytical Biochemistry (1996), vol. 233, pp. 124-129.*
International Search Report and Written Opinion from PCT/IN2014/000293 dated Mar. 2, 2015 (4 pages).
Ajay Kumar, "A Versatile Solid Phase Method for the Synthesis of Masked 3'-Thiol Group Containing Oligonucleotides", Nucleosides and Nucleosides, vol. 12, No. 10, pp. 1047-1059, 1993.
Kotikam Venubabu, et al, "Synthesis and Properties of 2'-O[R- and S-(2-amino-3-methoxy)propyl] (R-AMP and S-AMP) Nucleic Acids", Tetrahedron, Elsevier Science Publishers, vol. 69, No. 31, May 29, 2013.

* cited by examiner

*Primary Examiner* — Patrick Lewis
(74) *Attorney, Agent, or Firm* — Blank Rome LLP

(57) ABSTRACT

The present invention provides novel chiral serinyl functionalized tethered oligunucleotides i.e. R/S serinyl functionalized tethered oligonucleotides and the process of preparation thereof. Specifically, the present invention provides a modified nucleoside unit containing the R/S serinyl derivative at 2' of the sugar unit which is introduced in a nucleotide sequence. Also, capping of the oligonucleotides with abasic serinyl derivative to render the nuclease stability to the oligonucleotiedds is also disclosed. The chiral serinyl functionalized tethered oligonucleotides, 2'-O-[R/S-(2-amino-3-methoxy)propyl] nucleic acids with both '3- and 5'-ends capped with two units of abasic serine have antisense activity against the miRNA.

18 Claims, 4 Drawing Sheets

SEQUENCE LISTING

<160> NUMBER OF SEQ ID NOS: 20

<210> SEQ ID NO 1
<211> LENGTH: 18
<212> TYPE: DNA
<213> ORGANISM: Artificial Sequence
<220> FEATURE:
<223> OTHER INFORMATION: Oligomer

<400> SEQUENCE: 1
cctcttacct cagttaca                                                  18

<210> SEQ ID NO 2
<211> LENGTH: 18
<212> TYPE: DNA
<213> ORGANISM: Artificial Sequence
<220> FEATURE:
<223> OTHER INFORMATION: U-MOE  (2'-O-methoxyethyl uridine) at 15th
      position.

<400> SEQUENCE: 2
cctcttacct cagtuaca                                                  18

<210> SEQ ID NO 3
<211> LENGTH: 18
<212> TYPE: DNA
<213> ORGANISM: Artificial Sequence
<220> FEATURE:
<223> OTHER INFORMATION: U S-AMP (2'-O-[S-(2-amino-3-methoxy)propyl
      uridine) at 15th position.

<400> SEQUENCE: 3
cctcttacct cagtuaca                                                  18

<210> SEQ ID NO 4
<211> LENGTH: 18
<212> TYPE: DNA
<213> ORGANISM: Artificial Sequence
<220> FEATURE:
<223> OTHER INFORMATION: U R-AMP  (2'-O-[R-(2-amino-3-methoxy)propyl
      uridine ) at 15th position .

<400> SEQUENCE: 4
cctcttacct cagtuaca                                                  18

<210> SEQ ID NO 5
<211> LENGTH: 18
<212> TYPE: DNA
<213> ORGANISM: Artificial Sequence
<220> FEATURE:
<223> OTHER INFORMATION: UMOE (2'-O-methoxyethyl uridine)  at 10 th &
      15 th positon.

<400> SEQUENCE: 5
cctcttaccu cagtuaca                                                  18

<210> SEQ ID NO 6
<211> LENGTH: 19
<212> TYPE: DNA
<213> ORGANISM: Artificial Sequence
<220> FEATURE:
<223> OTHER INFORMATION: U S-AMP (2'-O-[S-(2-amino-3-methoxy)propyl
      uridine) at 10 th &15th position.

<400> SEQUENCE: 6
cctcttaccu scagtuaca                                                 19

<210> SEQ ID NO 7
<211> LENGTH: 18
<212> TYPE: DNA
<213> ORGANISM: Artificial Sequence
<220> FEATURE:
<223> OTHER INFORMATION: UR-AMP   (2'-O-[R-(2-amino-3-methoxy)propyl
      uridine) at 10th & 15th position

```
<400> SEQUENCE: 7
cctcttaccu cagtuaca                                                18

<210> SEQ ID NO 8
<211> LENGTH: 15
<212> TYPE: DNA
<213> ORGANISM: Artificial Sequence
<220> FEATURE:
<223> OTHER INFORMATION: Oligomer nucleotide

<400> SEQUENCE: 8
tttttttttt ttttt                                                   15

<210> SEQ ID NO 9
<211> LENGTH: 15
<212> TYPE: DNA
<213> ORGANISM: Artificial Sequence
<220> FEATURE:
<223> OTHER INFORMATION: U-MOE  (2'-O-methoxyethyl uridine)   at 14th &
      15th position

<400> SEQUENCE: 9
tttttttttt tttuu                                                   15

<210> SEQ ID NO 10
<211> LENGTH: 15
<212> TYPE: DNA
<213> ORGANISM: Artificial Sequence
<220> FEATURE:
<223> OTHER INFORMATION: US-AMP (2'-O-[S-(2-amino-3-methoxy)propyl
      uridine) at 14th & 15th position.

<400> SEQUENCE: 10
tttttttttt tttuu                                                   15

<210> SEQ ID NO 11
<211> LENGTH: 15
<212> TYPE: DNA
<213> ORGANISM: Artificial Sequence
<220> FEATURE:
<223> OTHER INFORMATION: U R-AMP   (2'-O-[R-(2-amino-3-methoxy)propyl
      uridine) at 14h & 15 th position

<400> SEQUENCE: 11
tttttttttt tttuu                                                   15

<210> SEQ ID NO 12
<211> LENGTH: 18
<212> TYPE: DNA
<213> ORGANISM: Artificial Sequence
<220> FEATURE:
<223> OTHER INFORMATION: oligomer nucleotide

<400> SEQUENCE: 12
cctcttacct cagttaca                                                18

<210> SEQ ID NO 13
<211> LENGTH: 18
<212> TYPE: DNA
<213> ORGANISM: Artificial Sequence
<220> FEATURE:
<223> OTHER INFORMATION: Capping of oligomer with S-amidite at 3'-5'.

<400> SEQUENCE: 13
cctcttacct cagttaca                                                18
```

```
<210> SEQ ID NO 14
<211> LENGTH: 18
<212> TYPE: DNA
<213> ORGANISM: Artificial Sequence
<220> FEATURE:
<223> OTHER INFORMATION: Capping of oligomer with two S-amidite at
      3'-5'.

<400> SEQUENCE: 14
cctcttacct cagttaca                                                  18

<210> SEQ ID NO 15
<211> LENGTH: 18
<212> TYPE: DNA
<213> ORGANISM: Artificial Sequence
<220> FEATURE:
<223> OTHER INFORMATION: oligomer nucleotide

<400> SEQUENCE: 15
cctcttacct cagttaca                                                  18

<210> SEQ ID NO 16
<211> LENGTH: 18
<212> TYPE: DNA
<213> ORGANISM: Artificial Sequence
<220> FEATURE:
<223> OTHER INFORMATION: Capping of oligomer with S-amidite at 3'-5'.

<400> SEQUENCE: 16
cctcttacct cagttaca                                                  18

<210> SEQ ID NO 17
<211> LENGTH: 18
<212> TYPE: DNA
<213> ORGANISM: Artificial Sequence
<220> FEATURE:
<223> OTHER INFORMATION: Capping of oligomer with two S-amidite at
      3'-5'.

<400> SEQUENCE: 17
cctcttacct cagttaca                                                  18

<210> SEQ ID NO 18
<211> LENGTH: 22
<212> TYPE: DNA
<213> ORGANISM: Artificial Sequence
<220> FEATURE:
<223> OTHER INFORMATION: Locked nucleotide Sequence: 4 LNA modification
      on Cysteine reidue at position 2 ,5 12 & 20.

<400> SEQUENCE: 18
tcaacatcag tctgataagc ta                                             22

<210> SEQ ID NO 19
<211> LENGTH: 22
<212> TYPE: DNA
<213> ORGANISM: Artificial Sequence
<220> FEATURE:
<223> OTHER INFORMATION: AMO-1 (anti-miR oligonucleotide)

<400> SEQUENCE: 19
ucaacaucag ucugauaagc ua                                             22
```

```
<210> SEQ ID NO 20
<211> LENGTH: 21
<212> TYPE: DNA
<213> ORGANISM: Artificial Sequence
<220> FEATURE:
<223> OTHER INFORMATION: U R-AMP    (2'-O-[R-(2-amino-3-methoxy)propyl
      uridine) at 1,7,13 , 21 th position And Capping od modidies
      oligomer withtwo S-amidite at 3'-5'.

<400> SEQUENCE: 20
ucaacaucag ucugauagcu a                                              21
```

2'/3'/5'-(R/S)-SERINYL FUNCTIONALIZED OLIGONUCLEOTIDES

CROSS-REFERENCE TO RELATED APPLICATIONS

This is a US 371 application from PCT/IN2014/000293 filed May 2, 2014, which claims priority to India Application No. 1308/DEL/2013 filed May 3, 2013, the technical disclosures of which are hereby incorporated herein by reference.

FIELD OF THE INVENTION

The present invention provides novel chiral serinyl functionalized tethered oligonucleotides i.e. R/S serinyl functionalized tethered oligonucleotides. Further, the invention relates to stereospecific introduction of R/S serinyl derivatives namely [R/S-(2-amino-3-methoxy)propyl] (R-AMP and S-AMP) in the middle of the sequence of oligonucleotide. The invention also provides phosphoramidite of abasic serinyl derivative R/S-serinyl amidite, R/S-(S amidite) and protection of oligonucleotide by capping the ends with R/S-S derivative.

BACKGROUND OF THE INVENTION

Synthetic antisense or siRNA (small interfering) oligonucleotides as gene silencing agents inhibit viral replication and expression of disease-causing genes based on the simple concept of nucleic acid sequence recognition via Watson-Crick hydrogen bonding by a complementary base sequence. The 2'-O-methoxyethyl substituted antisense oligonucleotides (MOE-AONs) are currently being studied in several ongoing clinical trials and have shown excellent safety profiles. The success of MOE-AONs was attributed to the gauche interactions of vicinal 2'-O— and the methoxy-substitution, thereby imparting favorable preorganization, favoring the hydration of DNA:RNA duplex minor groove and protecting against hydrolytic cleavage due to steric hindrance in the minor groove. In spite of the high thermal stability of the duplexes containing MOE-AONs ($\Delta Tm \approx 1°$ C./MOE unit), a large difference between their $IC_{50}$ and the $ED_{50}$ values was observed. The reason for this difference could be primarily arising from degradation of the antisense oligonucleotides (AONs) under physiological conditions and it is evident that it is of interest to reduce this difference and to optimize the therapeutic value of MOE-AONs. This should indeed be achievable by blocking the hydrolytic active site of the phosphodiesterase enzymes without compensating the target recognition ability of MOE-AONs. Antisense drugs are being researched to treat cancers (including lung cancer, colorectal carcinoma, pancreatic carcinoma, malignant glioma and malignant melanoma), diabetes, Amyotrophic lateral sclerosis (ALS), Duchenne muscular dystrophy and diseases such as asthma, arthritis and pouchitis with an inflammatory component.

U.S. Pat. No. 4,503,252 discloses the method for the synthesis of serinol comprising reacting 1,3-dimethoxy-isopropylchloride with excess ammonia by heating to form 1,3-dimethoxy-isopropylamine and subsequently converting this intermediate to serinol by refluxing it with aqueous hydrochloric acid. Selective alkylation of uridine at 2'-position such as treatment of uridine with alkyl halides using DBTO or by employing 3',5'-O- and N-protected uridine in reactions with alkyl halides reported by Martin, P. in Helv. Chim. Acta, 1995, 78, 486. Saneyoshi, H in M. J. Org. Chem. 2005, 70, 10453 describes the reaction of appropriately protected ribonucleoside derivatives with acrylonitrile in t-BuOH in the presence of $Cs_2CO_3$ gave 2'-O-cyanoethylated ribonucleoside derivatives in excellent yields, which were converted by a successive selective deprotection/protection strategy to 2'-O-cyanoethylated 5'-O-dimethoxytritylribonucleoside 3'-phosphoramidite derivatives in high yields. In addition, it provides that introduction of a cyanoethyl group into the 2'-position of RNA resulted in significant increase of nuclease resistance toward snake venom and bovine spleen phosphodiesterases. Additionally, Legorburu, U in Tetrahedron, 1999, 55, 5635 describes conversion of uridine into 2'-O-(2-methoxyethyl) uridine and 2'-O-(2-methoxyethyl) cytidine. Manoharan, M. et al. J. Org. Chem. 1999, 64, 6468 reported N-(2-Cyanoethoxycarbonyloxy) succinimide as new reagent for protection of amino groups in oligonucleotides, Lecubin F. in journal of Nucleosides Nucleotides Nucleic Acids, 2003 May-August; 22(5-8): 1281-4 discloses synthesis and triplex binding properties of oligonucleotides containing a novel nucleobase, whereas triple helix hybridization studies were examined by means of thermal denaturation experiments with a 26-mer DNA duplex containing the AT inverted base pair. Further Yuichi Nakamura in Org. Lett., 2013, 15 (2), pp 322-325 Publication: Dec. 26, 2012 describes siladenoserinols a-l as sulfonated serinol derivatives from a tunicate as inhibitors of p53-hdm2 interaction, a promising target for cancer chemotherapy.

Recently, there have been some fine efforts in this direction to combine the structural aspects of locked nucleic acids (LNA) with MOE-AONs (S/R-cMOE, S/R cEt). Indeed, these additional modifications stabilize modified LNA against enzymatic cleavage improving their potency mainly by AONs stabilization to potential in vivo degradation. It was further shown by crystal structural data for the duplex containing a single unit of cMOE that the constrained LNA framework, substituted with a —$CH_2OMe$ or Me groups, brings these substitutions close to the phosphate, preventing, for steric reasons, the metal binding required for the hydrolytic cleavage. Furthermore, the efficiency of both cMOE diastereoisomeric derivatives is similar in blocking the enzyme activity. The cost of LNAs, together with the additional synthetic steps in the preparation of functionalized LNA derivatives, probably prevents their use as therapeutic agents. LNA is also known to show hepatotoxicity. The stability of MOE and LNA analogs to hydrolytic enzymes is low, and requires phoshorothioates for further stabilization against enzymatic degradation.

The synthetic approach for modifications at 3'- and 5'-end as well as at 2'-position is easy and scalable as compared to the other alternatives such as combining LNA and MOE strategies. The LNA/MOE combination leads to cMOE and cEt modifications do stop degradation of oligomers but without chiral discrimination, completely depending upon steric bulk of bicylic system. The above synthesis further involves several steps and separation of diastereomers.

To overcome the above drawbacks, the present inventors have synthesized new serinyl compounds characterized by the presence of a positively charged amino functionality in conjunction with the methoxy substituent on the 2'-O-alkyl chain, in particular, due to electrostatic repulsions, a positively charged amino functionality may potentially displace the metal ion, required for the hydrolytic cleavage. Further, the stereospecific addition of protonable amino group to the 2'-O-methoxyalkyl component preferentially resists hydrolytic cleavage by enzymes without use of phosphorothioate. Advantageously the presence of an ammonium group on modified MOEs improves the hydration in the minor groove enhancing the stabilization of the duplex.

Therefore the present inventors have prepared novel 2'/3'/5'-R/S serinyl functionalized nucleic acids to save ODNs (oligodeoxyribonucleotides) from degradation without derivatization at phosphorus; and also to make better recognition strength of oligonucleotides, because the phosphorothioate analogs incur loss in binding strength to target RNA.

OBJECTS OF THE INVENTION

The main object of the present invention is to provide novel chiral serinyl functionalized tethered oligonucleotides and the process of preparation thereof.

Another object of the present invention it to provide novel 2'/3'/5'-(R/S) serinyl functionalized tethered oligonucleotides which are resistant to degradation.

Another object of the present invention is to provide stereospecific synthesis of (S)-benzyl (1-methoxy-3-((trimethylsilyl)oxy)propan-2-yl)carbamate (S-3).

Another object of the present invention is to provide stereospecific synthesis of (R)-benzyl (1-((tert-butyldimethylsilyl)oxy)-3-methoxypropan-2-yl)carbamate (R-5)

Another object of the present invention is to provide a process for preparing (S-3) and (R-5) which gives product with high yield and purity.

SUMMARY OF THE INVENTION

The present invention provides a novel chiral serinyl functionalized tethered oligonucleotides having Formula I,

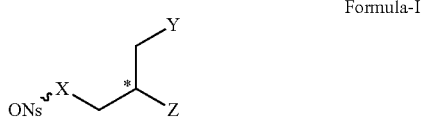

Formula-I wherein, X is selected from the group consisting of 'O' or 'S';

Y is selected from the group consisting of OH, SH, OMe, SMe or OP;

Z is selected from the group consisting of $NH_2$, NHR, $NHR_2$, guanidine or NHP; where R is ($C_1$-$C_{10}$) alkyl, heteroaryl, aryl, alkyl aryl and P is protecting group selected from the group consisting of Cbz, TFA, DMT, TBS, TMS; where ONs is oligonucieotide(s).

The chirality of the tethered oligonucleotides is either R or S.

An aspect of the present invention provides the process for stereospecific synthesis of enantiomeric amino alcohol tethers i.e. chiral serinol derivatives [R/S-(2-amino-3-methoxy) propanol tethers (R-AMP and S-AMP) from L-serine and stereospecific introduction of the same in the middle of the oligonucleotide sequence.

Another aspect of the present invention provides a process to obtain phosphoramidite of serinyl derivative S/R-serinyl (S/R-S) amidite. Further, it furnishes protection of oligonucleotide by capping the 3' and 5'-ends with R/S serinyl derivative such as S-S unit and R-S unit.

Data shown is the mean±SEM of three independent experiments. *p-value<0.05, **p-value<0.001 indicates significant statistical difference between the oligonucleotide treated and vector control.

Figure 5:
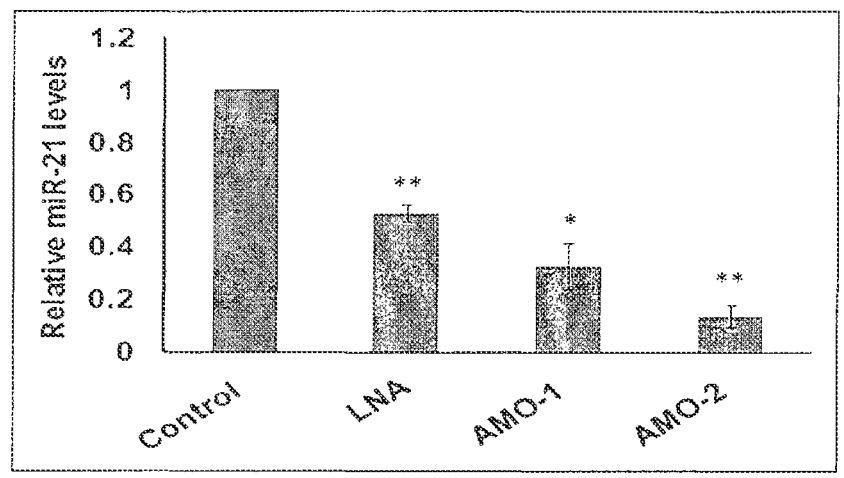
Figure 6:
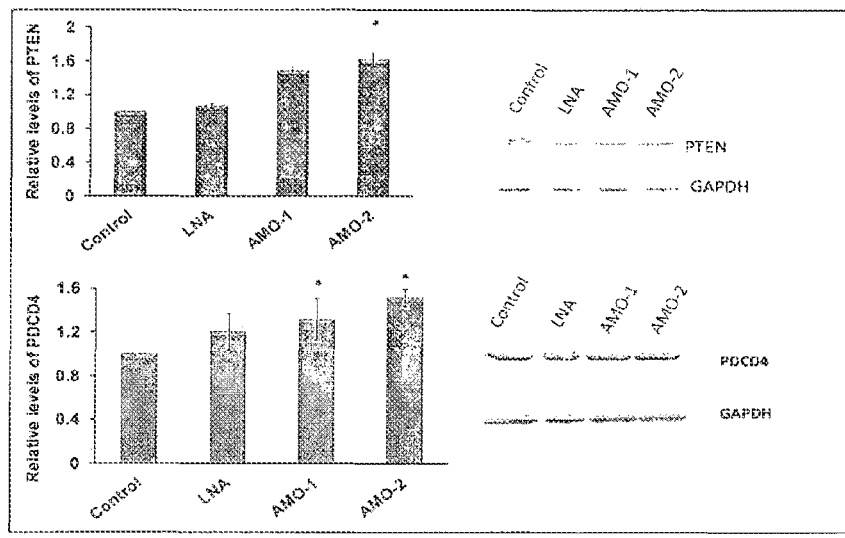

FIG. 5 depicts specific inhibition of miR-21 by various AMOs. LNA was taken as positive control. AMO-2 causes >80% inhibition of miR-21 as compared to AMO-1 which causes ~60% of down regulation FIG. 6 depicts Western Blot analysis shows an inverse correlation of miR-21 targets PTEN and PDCD4 in response to AMOs. The most potent AMO was AMO-2. LNA was taken as positive control and GAPDH as the loading control. Data shown is the mean±SEM of three independent experiments. *p-value<0.05, **p-value<0.001 indicates significant statistical difference between the oligonucleotide treated and untreated control.

Figure 7:
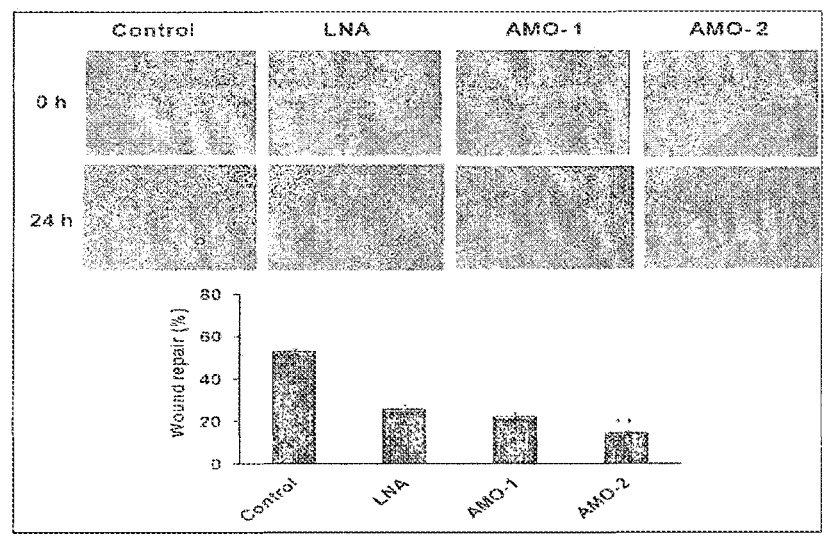

FIG. 7 depicts representative image of in-vitro scratch assay in MCF-7 cell line at 0 hrs and 24 hrs after wound scratch. Knockdown of miR-21 by LNA/AMO-1/AMO-2 suppresses the migration capacity as compared to the untreated control. Wound repair in case of AMO-1 and AMO-2 at 50 nM is inhibited as compared to untreated control. LNA is taken as a positive control.

Figure 8:
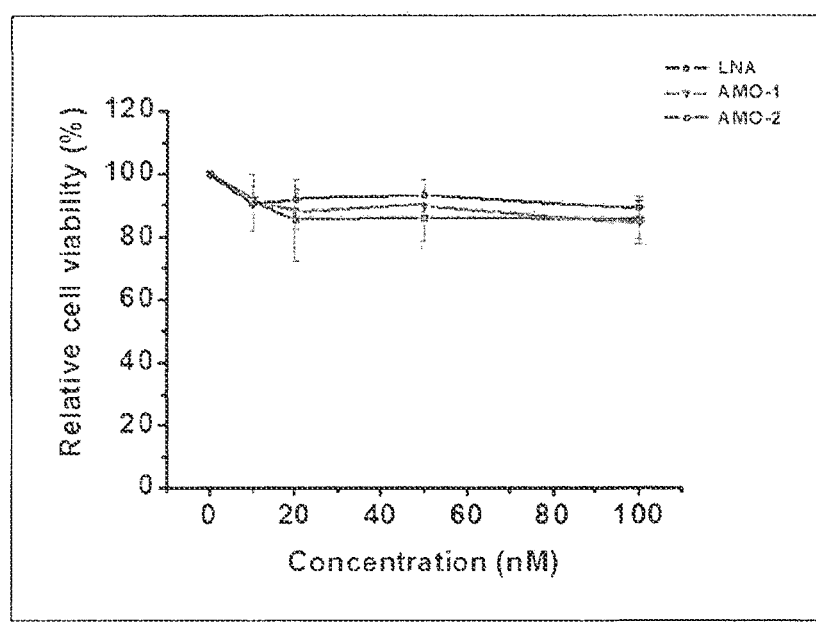

FIG. 8 depicts effect of antisense treatments on cell viability. Cells were transfected with different concentrations (10 to 100 nM) of LNA, AMO-1 and AMO-2 for 24 hrs. Cell viability was measured by MTT assay as compared to the untreated control. The viability of the cells remains unaffected upto 100 nM of the three oligonucleotides thus exhibiting no measurable cytotoxicity. Data shown is the mean±SEM of three independent experiments.

ABBREVIATIONS USED

ODNs: oligodeoxyribonucleotides
ONs: oligonucleotides
R-AMP: R-(2-amino-3-methoxy)propyl
S-AMP: S-(2-amino-3-methoxy)propyl
MOE-AONs: 2'-O-methoxyethyl substituted antisense oligonucleotides
AONs: antisense oligonucleotides
LNA: locked nucleic acids
S: S/R-serinyl
SVPD: snake venom phosphodiesterase enzyme
DMT: Dimethoxytrityl
TFA: Trifluoroacetic acid DIPEA: N,N-Diisopropylethylamine
TBDPS: tertiarybutyldiphenylsilyl
TBS: tertiarybutyldimethylsilyl
TMS: Trimethylsilyl
DCM: Dichloromethane
Cbz: Carbonyloxybenzyl
R-2: (R)-benzyl (1-hydroxy-3-methoxypropan-2-yl)carbamate
S-3: (S)-benzyl (1-methoxy-3-((trimethylsilyl)oxy)propan-2-yl)carbamate
R-4: (R)-benzyl (1-((tert-butyldimethylsilyl)oxy)-3-hydroxypropan-2-yl)carbamate
R-5: (R)-benzyl (1-((tert-butyldimethylsilyl)oxy)-3-methoxypropan-2-yl)carbamate
S-7/R-8: 2'-O-functionalization of 2,2'-anhydrouridine
(S-9/R-10): 5'-O-DMT protection of 2'-O-functionalized uridine
S-11/R-12): Change of amine-protecting group at the 2'-tether
(S-13/R-14): serinyl phosphoramidite derivatives
$U^{R-AMP}$: 2'-O-R-(2-amino-3-methoxypropyl)uridine
$U^{S-AMP}$: 2'-O-S-(2-amino-3-methoxypropyl)uridine
$U^{MOE}$: 2'-O-(2-methoxyethyl)uridine In sequences, all uppercase letters denote "deoxyribonucleotides" and lower case letters denote "2'-O-methylribonucleotides".

DETAILED DESCRIPTION OF THE INVENTION

The invention will now be described in detail in connection with certain preferred and optional embodiments, so that various aspects thereof may be more fully understood and appreciated.

The terms "R/S-(2-amino-3-methoxy)propanol", "chiral serinyl derivatives", "enantiomeric amino alcohol tethers", [R/S-(2-amino-3-methoxy)propanol] tethers', (R-AMP and S-AMP), 'R/S serinol derivatives', 'S-3 and R-5' 'TMS-ethers' and 'TBS-ether' as referred herein in the entire specification are used interchangeably and hence the person skilled in the art will appreciate the same as such.

The novelty of the present invention lies in the novel chiral serinyl functionalized tethered oligonucleotides and the process of preparation thereof.

The main embodiment of the present invention provides a novel chiral serinyl functionalized tethered oligonucleotides having Formula I,

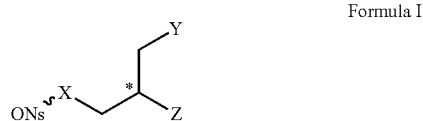

Formula I wherein,
X is selected from the group consisting of 'O' or 'S';
Y is selected from the group consisting of OH, SH, OR, SR or OP, $NH_2$, NHR, $NR_2$ where R is ($C_1$-$C_{10}$) alkyl, heteroaryl, aryl, alkyl aryl and P is a protecting group selected from the group consisting of Cbz, TFA, DMT, TBS, TMS;
Z is selected from the group consisting of $NH_2$, NHR, $NHR_2$, guanidine or NHP or OR, SR; where R is H, ($C_1$-$C_{10}$) alkyl, heteroaryl, aryl, alkyl aryl and P is a protecting group selected from the group consisting of Cbz, TFA, DMT, TBS, TMS, where "ONs" is oligonucleotide(s), for use in inhibiting miRNA.

In another embodiment of the present invention, X is O.
In another embodiment of the present invention, Y is OR where R is ($C_1$-$C_{10}$) alkyl, heteroaryl, aryl, alkyl aryl.
In another embodiment of the present invention, Z is NHR where R is H or ($C_1$-$C_{10}$) alkyl, heteroaryl, aryl, alkyl aryl.
In yet another embodiment of the present invention, wherein:
X is O;
Y is OH or OMe;
Z is $NH_2$;
R is H;
In another embodiment of the present invention, the chirality of tether in oligonucleotides is either R or S.
In another embodiment of the present invention, the oligonucleotides are selected from DNA or RNA or their derivatives.
In another embodiment of the present invention, the chiral serinyl functionalized tethered oligonucleotides are obtained from the 2'-O-functionalization of nucleic acids with R-(2-amino-3-methoxy)propyl] (R-AMP) and S-(2-amino-3-methoxy)propyl] (S-AMP) tethers and incorporation into ONs.
In another embodiment of the present invention, the 2' of the ribose sugar in nucleic acids is functionalized with R/S serinyl derivative, (S-AMP) unit and/or (R-AMP) units and introduced in the oligonucleotide sequence either continuously or evenly dispersed throughout the sequence.
In another embodiment of the present invention, the chiral serinyl functionalized phosphoramidite are introduced at either 3'- or 5'-ends of a nucleotide sequence with R/S serinyl derivative, (S)-unit.
In another embodiment of the present invention, the modified nucleoside containing the R/S serinyl derivative at 2' of the sugar unit is introduced at specific positions in a nucleotide sequence selected from 3', 5' and central region.
Yet another embodiment of the invention provides a process for preparing chiral serinyl functionalized tethered oligonucleotides of Formula I, comprising the steps of;
a) Preparing R/S-serinyl amidite R/S-(S amidite) and
b) introducing S-serinyl (S) capping of the oligonucleotide with S-amidite at 3'- and 5'-positions to obtain 3'- and 5'-protected (S)-chiral serinyl functionalized tethered oligonucleotides.

Another embodiment of the present invention provides a process for preparing (S)-serinyl functionalized tethered oligonucleotides of formula I, comprising the steps of;
a) protecting the alcohol group of the serine ester (1) to obtain DMT-ether using dimethoxytrityl chloride, followed by ester reduction to alcohol to furnish (1a) followed by the changing the amino protecting group of (1a) from —NH-Cbz to —NH-TFA using ethyltrifluoro acetate and subsequent phosphitylation to obtain the S amidite (1b); and

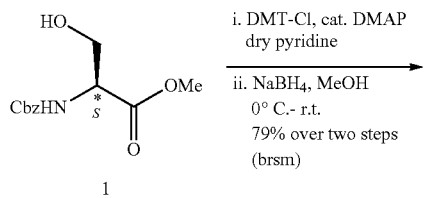

-continued

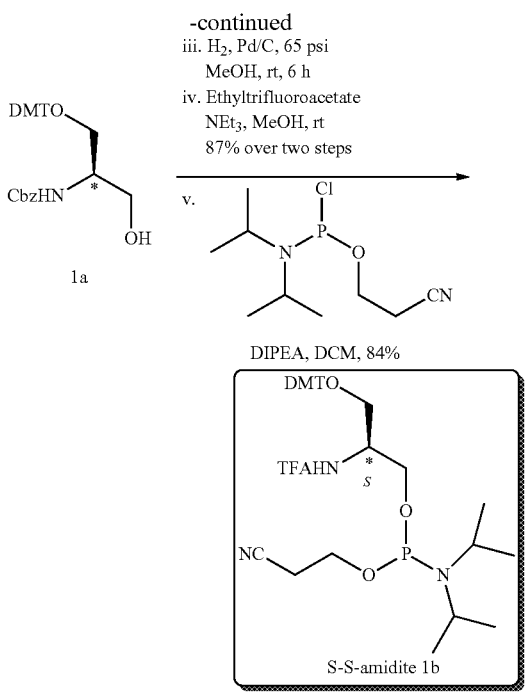

iii. H₂, Pd/C, 65 psi
MeOH, rt, 6 h
iv. Ethyltrifluoroacetate
NEt₃, MeOH, rt
87% over two steps v.

DIPEA, DCM, 84% b) introducing abasic serinyl (S) capping to the oligonucleotide with S-S-amidite at 3'- and 5'-positions to obtain (S)-serinyl functionalized tethered oligonucleotides.

Another embodiment of the present invention provides a process for preparing R/S chiral serinyl functionalized tethered oligonucleotides of formula I, comprising the steps of:
a) stereospecifically synthesizing enantiomeric serinol derivatives [R/S-(2-amino-3-methoxy) propanol tethers (R-AMP and S-AMP) from the natural amino acid L-serine;
b) functionalization of anhydrouridine by reacting with [R/S-(2-amino-3-methoxy) propanol tethers followed by phosphitylation to obtain 2'-O-R/S-(2-amino-3-methoxypropyl)uridine amidite ($U^{R-AMP}$ and $U^{S-AMP}$ amidite); and
c) introducing S-serinyl (S) capping of the oligonucleotide with S-amidite (1b, Scheme 1) at 3'- and 5' positions to obtain R/S chiral serinyl functionalized tethered oligonucleotides.

In another embodiment of the present invention, [R/S-(2-amino-3-methoxy) propanol tethers (R-AMP and S-AMP) are (S)-benzyl (1-methoxy-3-((trimethylsliyl)oxy)propan-2-yl)carbamate (S-3) or, (R)-benzyl (1-((tert-butyldimethylsilyl)oxy)-3-methoxypropan-2-yl)carbamate (R-5).

Another embodiment of the present invention provides a process for preparing (S)-benzyl (1-methoxy-3-((trimethylsilyl)oxy)propan-2-yl)carbamate (S-3), comprising the steps of:
a) O-methylation of N-Cbz-protected-L-serine methyl ester 1 using silver oxide and methyl iodide followed by reduction to obtain, (R)-benzyl (1-hydroxy-3-methoxypropan-2-yl)carbamate (R-2), and
b) transforming (R)-benzyl (1-hydroxy-3-methoxypropan-2-yl)carbamate (R-2) into (S)-benzyl (1-methoxy-3-((trimethylsilyl)oxy)propan-2-yl)carbamate (S-3) using trimethylsilylchloride (TMS-Cl).

Another embodiment of the present invention provides a process for preparing (R)-benzyl (1-((tert-butyldimethylsilyl)oxy)-3-methoxypropan-2-yl)carbamate (R-5), comprising the steps of:
a) protecting serine ester 1 with tertiarybutyldimethylsilyl ether (TBS) followed by reduction to get (R)-benzyl (1-((tert-butyldimethylsilyl)oxy)-3-hydroxypropan-2-yl)carbamate (R-4), and,
b) methylation of free hydroxyl group in (R)-benzyl (1-((tert-butyldimethylsilyl)oxy)-3-hydroxypropan-2-yl)carbamate (R-4) to give, (R)-benzyl (1-((tert-butyldimethylsilyl)oxy)-3-methoxypropan-2-yl)carbamate (R-5).

Yet another embodiment of the invention provides a process for stereospecific synthesis of both the enantiomeric amino alcohol tethers at 2'-O-position of nucleosides i.e. chiral serinyl derivatives 2'-O-[R/S-(2-amino-3-methoxy) propyl uridine ($U^{R-AMP}$ and $U^{S-AMP}$) from 2,2'-anhydouridine. The stereospecific projection of amino substituent in the minor groove while interacting with the chiral environment of the enzyme would be energetically different for two isomers and therefore the resultant stability towards hydrolytic cleavage could be different.

Accordingly, the invention provides the process for synthesis of protected [S/R-(2-amino-3-methoxy) propanol] (i.e. S-3) and (i.e. R-5) starting from the same chiral source, i.e. protected L-serine, by altering the sequence of reactions to obtain the enantiomeric tethers (S)-benzyl (1-methoxy-3-((trimethylsilyl)oxy)propan-2-yl)carbamate (S-3) and (R)-benzyl (1-((tert-butyldimethylsilyl)oxy)-3-methoxypropan-2-yl)carbamate (R-5) having suitable activation/protection, as shown in below Scheme 1.

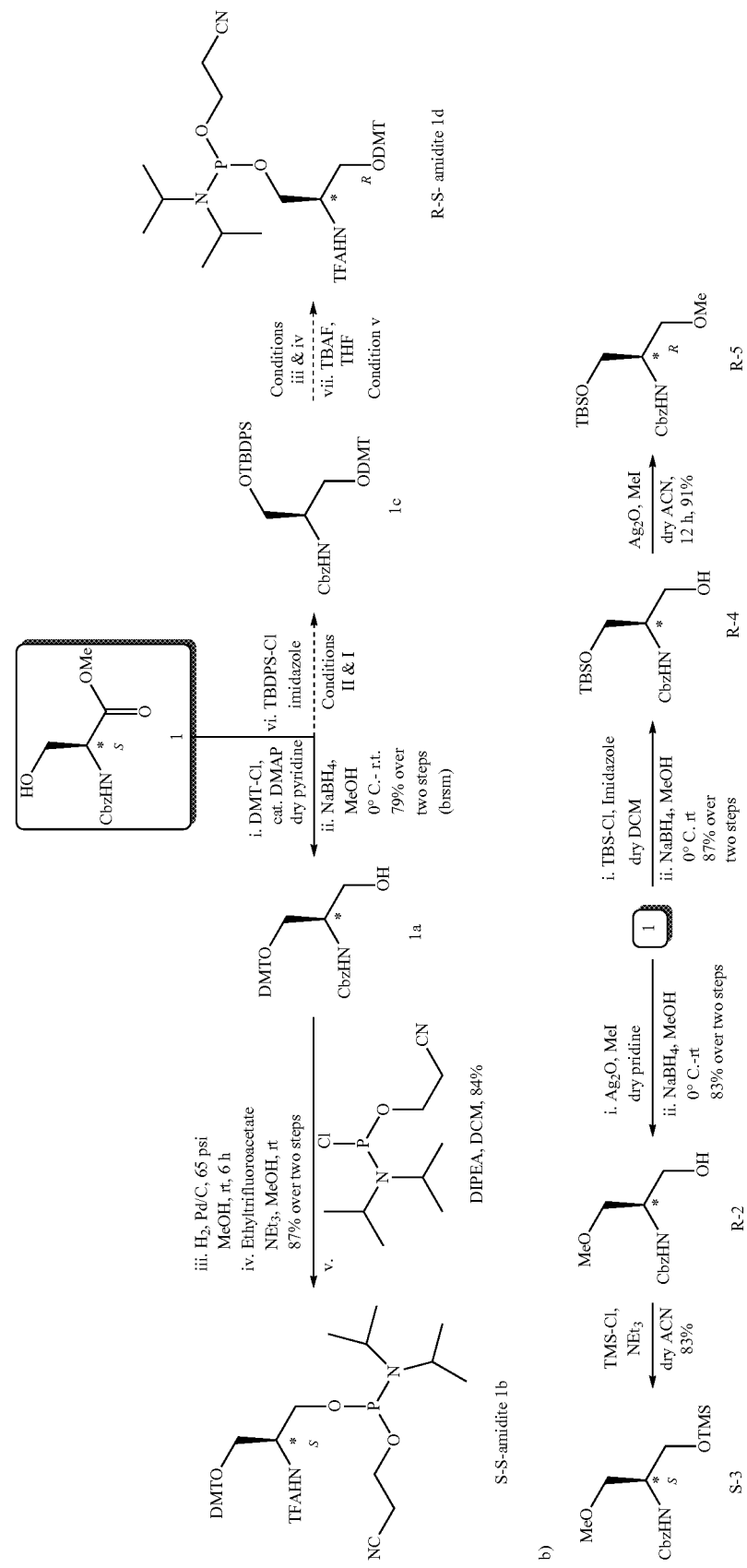
Scheme 1: Synthesis of R/S-serinyl derived R/S-S amidites for capping the ONs (a) and protected/activated [R/S-(2-amino-3-methoxy)propanol (S/R-AMP) tethers (b).

In accordance with the above process, the yield of protected chiral intermediates and the final product i.e. (S-3) and (R-5) was obtained in the range of 80% to 99%.

The (S)-benzyl (1-methoxy-3-((trimethylsilyl)oxy)propan-2-yl)carbamate (S-3) and (R)-benzyl (1-((tert-butyldimethylsilyl)oxy)-3-methoxypropan-2-yl)carbamate (R-5) thus obtained are further converted into their corresponding 2'-O-(R-AMP)uridine ($U^{R-AMP}$) and 2'-O-(S-AMP)uridine ($U^{S-AMP}$) amidites (Scheme 4).

In another embodiment, the invention provides process for the conversion of L-serine (1) to its phosphoramidite derivative i.e. S-S amidite (1b) based on 2-amino-1,3-dihdroxypropyl (AmP) unit (1a), wherein the process comprising the steps of;

a) protecting the alcohol group of the serine ester (1) to obtain DMT-ether, followed by ester reduction to alcohol to furnish (1a), b) followed by the changing the amino protecting group of (1a) from —NH-Cbz to —NH-TFA and subsequent phsphitylation to obtain S-S amidite (1b) (cf Scheme 1a).

In yet another embodiment, the invention provides protection of oligonucleotide by capping the ends with R/S serinyl derivative (S) which is represented by Scheme 2.

SCHEME 2:

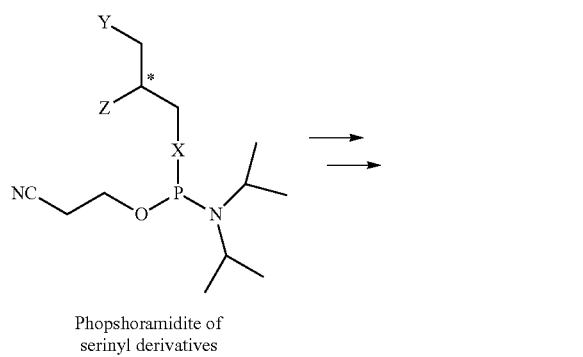

Phopshoramidite of
serinyl derivatives (S)$_n$-DNA-(S)$_n$
(S)$_n$-RNA-(S)$_n$
(S)$_n$-2'-OMeRNA-(S)$_n$ Protection of oligonucleotides by
capping the ends with R/S-serinyl derivatives X = O or S
Y = OH or SH
Z = NH$_2$ or NHR or guanidine
where R = alkyl/aryl where S = 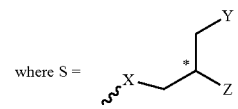

n = 1, 2, 3 . . . 10

The capping serinyl drivative chirality is either R or S

Particularly, the protection of oligonucleotide by capping or blocking the 3'- and 5'-ends towards hydrolytic cleavage of oligonucleotides. The introduction of the abasic serinyl (S) capping of the ONs via phosphodiester linkage at 3'- and 5'-ends also improves the degradation by hydrolytic enzymes.

SCHEME 3:

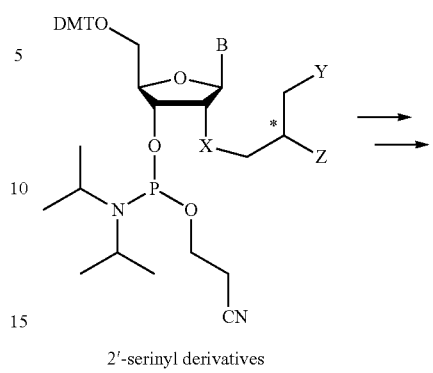

2'-serinyl derivatives

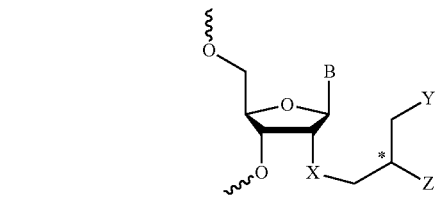

2'-serinyl-derivatives functionalized oligonucleotides
(Modified units in DNA/RNA/2'-OMe RNA)

X = O or S
Y = OH or OMe or SH or SME
Z = NH$_2$ or NHR or NR$_2$ or guanidine where R = alkyl/aryl  B = A/T/G/C/U The 2'-serinyl derivative chirality is either R or S In another embodiment, the invention provides protection of AONs containing S-AMP and R-AMP functionalization at 2'-O-position (Scheme 3), particularly the invention pertains to synthesis of protected 2'-O-[R/S-(2-amino-3-methoxy)propyl uridine phosphoramidite containing ($U^{R-AMP}/U^{S-AMP}$) as depicted in Scheme 4.

Scheme 4: Synthesis of protected 2'-O-[R/S(2-amino-3-methoxy)propyl uridine phosphoramidite (S-13 and R-14).

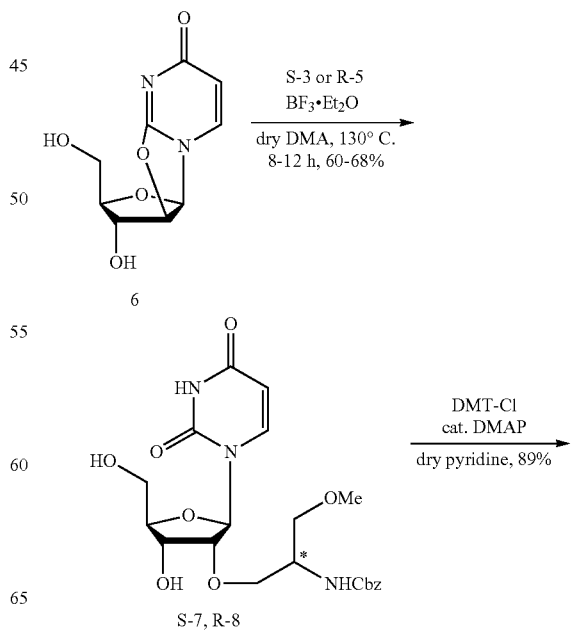

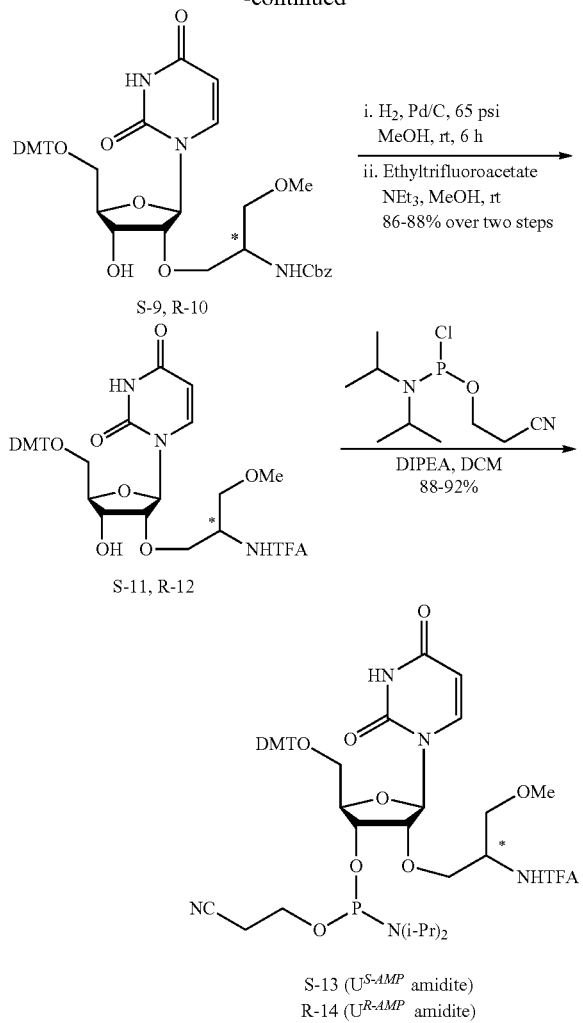

S-9, R-10 i. H₂, Pd/C, 65 psi
MeOH, rt, 6 h
ii. Ethyltrifluoroacetate
NEt₃, MeOH, rt
86-88% over two steps

S-11, R-12

DIPEA, DCM
88-92%

S-13 (U$^{S\text{-}AMP}$ amidite)
R-14 (U$^{R\text{-}AMP}$ amidite)

According to Scheme 4, the invention provides process for the synthesis of protected 2'-O-[R/S-(2-amino-3-methoxy)propyl uridine phosphoramidite by employing 2 equivalents of (S-AMP) or (S-3) and (R-AMP) or (R-5) tethers.

The synthesis of appropriately protected R-AMP and S-AMP phosphoramidite derivatives of uridine starting from 2,2'-anhydrouridine is represented in Scheme 4; wherein the process comprises BF₃— promoted 2,2'-anhydro ring opening strategy used by using trimethylsilylated alcohol as a nucleophile.

The detailed process for synthesis of 2'-O-[R/S(2-amino-3-methoxy)propyl uridine phosphoramidite comprises steps of;
a) reacting 2,2'-anhydrouridine with 2 equivalents of TMS-ethers (S)-benzyl (1-methoxy-3-((trimethylsilyl)oxy)propan-2-yl)carbamate or [S-3], or TBS-silyl ethers, (R)-benzyl (1-((tert-butyldimethylsilyl)oxy)-3-methoxypropan-2-yl)carbamate [R-5] to get the desired 2,2'-anhydro ring-opened products S-7 and R-8 with comparable yields (60, 68% respectively);
b) protecting 5' end of S-7 and R-8 compounds as —O-DMT ether to obtain 5'-O-DMT protected 2'-O-functionalized uridine S-9 and R-10 respectively;
c) deprotecting the N-Cbz protecting group of the 2'-O-functionalized uridine S-9 and R-10 by hydrogenation in presence of 10% Pd/C under pressure, followed by protecting the primary amino group to give trifluoroacetyl derivatives S-11 and R-12;
d) preparing phosphoramidite derivatives S-13 and R-14 by phosphitylation of S-11 and R-12, to be used in automated DNA synthesis.

In step c) of the instant process, the primary amino group is protected to give trifluoroacetyl derivatives S-11 and R-12 are suitable for solid-phase DNA synthesis protocols.

Additionally, it is demonstrated that S-AMP- and R-AMP-derivatized AONs stabilize duplexes as good as MOE and exhibit stereochemistry-dependent protection against hydrolysis by snake venom phosphodiesterase enzyme (SVPD).

In yet another preferred embodiment, the present invention provides modified nucleoside unit containing the R/S serinyl derivative at 2' of the sugar unit incorporated at 3', 5' or central region of the nucleotide sequences to obtain modified ONs of DNA, RNA, 2'-OMe RNA (Scheme 3).

EXPERIMENTATION

Further the phosphoramidites S-13 and R-14 were incorporated into sequences using increased coupling time (6 min) to yield the modified sequences and their mass analysis is represented in

TABLE 1

Table 1: Modified DNA sequences, their MALD1-TOF Mass analysis and biophysical evaluation by UV-T$_m$ (° C.) measurements[a]

| Sequences No.[b] | Mass Calcd | Mass Obsd | T$_m$ (° C.) RNA[c] |
|---|---|---|---|
| CCTCTTACCTCAGTTACA 15 | | | 56.6 |
| CCTCTTACCTCAGTU$^{MOE}$ACA 16 | 5429.9 | 5430.0 | 55.8 |
| CCTCTTACCTCAGTU$^{S\text{-}AMP}$ACA 17 | 5459.6 | 54602 | 56.2 |
| CCTCTTACCTCAGTU$^{R\text{-}AMP}$ACA 18 | 5459.6 | 5460.6 | 56.2 |
| CCTCTTACCU$^{MOE}$CAGTU$^{MOE}$ACA 19 | 5490.9 | 5492.7 | 57.4 |
| CCTCTTACCU$^{S\text{-}AMP}$CAGTU$^{S\text{-}AMP}$ACA 20 | 5549.0 | 5549.8 | 57.3 |
| CCTCTTACCU$^{R\text{-}AMP}$CAGTU$^{R\text{-}AMP}$ACA 21 | 5549.0 | 5551.4 | 57.5 |

[a]UV- T$_m$ values were measured by annealing 1 μM sequences with 1 μM cDNA/RNA in sodium phosphate buffer (0.01M, pH 7.2) containing 100 mM NaCl and is an average of three independent experiments. (Accuracy is ±0.5° C.)
[b]The upper case letters indicate unmodified DNA; U$^{MOE}$ denotes 2'-O-methoxyethyl uridine, U$^{S\text{-}AMP}$ and U$^{R\text{-}AMP}$ denote 2'-O-[S-(2-amino-3-mcnioxy)propyl and 2'-O-[R-(2-amino-3-methoxy)propyl uridine derivatives respectively.
[c]5'uguaacugagguaagagg was the complementary RNA sequence.

Figure 1:
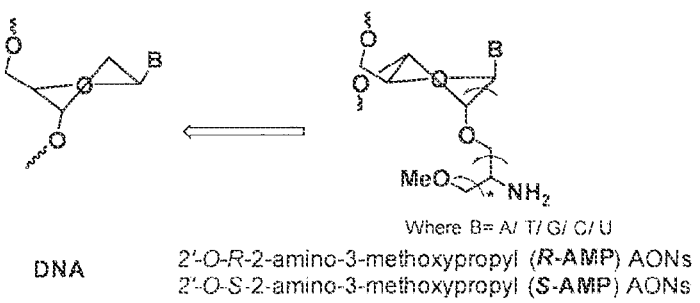
FIG. 1 depicts design of R-AMP and S-AMP.

The unmodified oligomers were synthesized using Bio-automation MM4 DNA synthesizer and commercially available phosphoramidite building blocks. According to Table 1, the site of the modified units in the sequences was decided so that these units were in the middle of the sequence (16-18, Table 1), were separated by 4-5 nucleosides (19-21, Table 1) or were at consecutive 3'end positions (23-25, FIG. 2). The AONs were purified by HPLC subsequent to ammonia treatment and characterized by MALDI-TOF mass spectrometric analysis. The thermal stability of DNA:RNA duplexes was evaluated using temperature dependent UV measurements and the results were comparable to U$^{MOE}$ containing oligomers (Table 1). The vicinal electronegative substituents, namely, O4', O2'- and 2-amino- and 3-methoxy- on the propyl chain at 2'-O-position of uridine would be expected to maintain the gauche orientations (FIG. 1) and would induce conformational change and hydration in the minor groove as is known for 2'-O-MOE derivatives and this might indeed be the case as the stability of the duplex structures was maintained.

Figure 2:
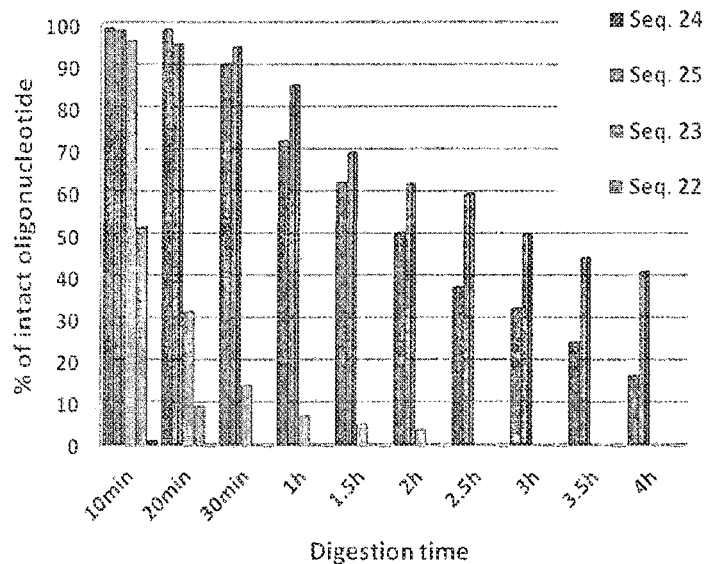
FIG. 2 depicts preferential protection of AONs containing 2'-O-S-AMP and 2'-O-R-AMP substituted uridine at 3'-24-25 (TTTTTTTTTTTTU$^{S\text{-}AMP}$U$^{S\text{-}AMP}$ 24, TTTTTTTTTTTTU$^{R\text{-}AMP}$U$^{R\text{-}AMP}$ 25) compared to native TTTTTTTTTTTTTT 22 and MOE-modified DNA TTTTTTTTTTTTTU$^{MOE}$U$^{MOE}$ 23.

In-Vitro Studies:

The inventors further explored the in-vitro studies regarding the protection of these newly synthesized oligomers tethered with $U^{S-AMP}$ and $U^{R-AMP}$ units against hydrolytic cleavage and compared the results with the $U^{MOE}$ tether. MOE is being developed as antisense therapeutic and is also finding newer applications in siRNA approach where only two terminal units are modified with MOE. Therefore the inventor synthesized a homothyminyl sequence 22 and modified it at the 3'-terminus with two consecutive units of $U^{MOE}$ or $U^{S-AMP}$ or $U^{R-AMP}$ to get sequences 23, 24 and 25 respectively (FIG. 2) and digested them with SVPD under conditions reported earlier. The products of the digestion were analysed by RP-HPLC and percent intact AON was plotted against time to understand the degradation pattern for all the oligomers (FIG. 2). The results clearly indicate the dependence of enzyme digestion in the presence of protonable amino group as charged species, as both the oligomers containing $U^{S-AMP}$ 24 and $U^{R-AMP}$ 25 are much more stable than the unmodified 22 and $U^{MOE}$-modified 23 sequences. The stereochemical influence of amino group of the AMP tethers in $U^{S-AMP}$ (24) and $U^{R-AMP}$ (25) AONs was clearly reflected in SVPD digestion experiment (cf FIG. 2).

According to the invention, the MOE-AONs were almost completely digested by SVPD at the end of 1 h. At the same time, almost 90% of R-AMP-AONs and 80% S-AMP-AONs were intact and were effectively able to resist the hydrolytic cleavage. Furthermore, 40% of R-tethered AON stereoisomer was still intact after 4 h and twice more stable than S-stereoisomer. In majority of the cases of achiral substituents studied so far, two types of crystal structures were observed where the 2'-O-substituent points toward 3'-terminus or toward 5'-terminus, introduction of chirality in the minor groove as in the case of 2'-O-R-AMP and 2'-O-S-AMP, should indeed restrict such structural features compared to the achiral, acyclic, alkyl substitution such as 2'-O-MOE. Instead, the chirality of said serinyl compounds, allowing a preferential protection against nucleases, would improve the therapeutic potency of these oligomers. The chirality effect on protection of AONs against digestive enzymes such as SVPD was also evaluated when currently therapeutically used, fully modified, stereorandom phosphorothioate oligonucleotides were synthesized in chirally pure form but without the synergistic effects on binding preferences.

Figure 3:
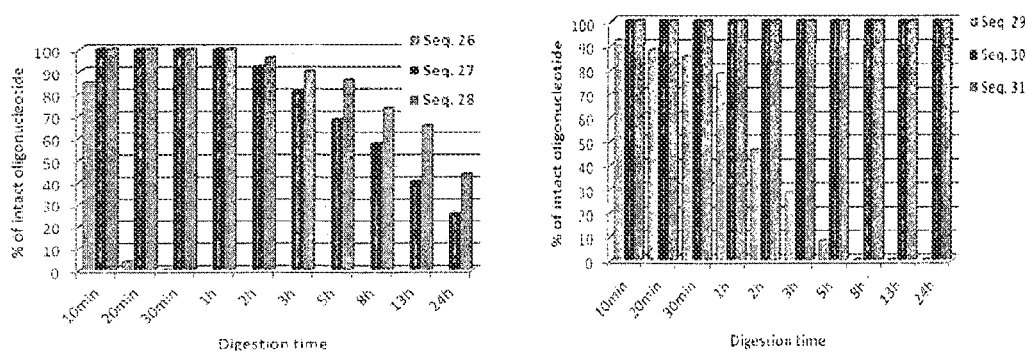
FIG. 3 depicts Protection of DMA (Seq. 26-28)/2'-OMe RNA (Seq. 29-31) AONs by capping both 3'- and 5'-ends with the abasic S derivative. DNA sequences: CCT CTT ACC TCA GTT ACA 26; S-CCT CTT ACC TCA GTT ACA-S 27, SS-CCT CTT ACC TCA GTT ACA-SS 28. 2'-OMe RNA sequences: cct ctt acc tca gtt aca 29; S-cct ctt acc tca gtt aca-S 30; SS-cct ctt acc tca gtt aca-SS 31, in all cases S is having S-stereochemistry.

The introduction of S amidite i.e. abasic serinyl derivative (Scheme 1a), was done at 3'- as well as 5'-end of the sequences (DNA sequence of CCT CTT ACC TCA GTT ACA 26-28) and 2'-OMe-RNA sequence cct ctt acc tca gtt aca (29-31) it was shown that these sequences were stable to hydrolytic cleavage even upto 24 h (FIG. 3). Thus, here, efficient synthesis of novel, chiral R/S-AMP-AONs is presented. The synergistic contribution of MOE and chiral amino substituents preserved the DNA:RNA duplex stability and their stereochemical dependent enzyme digestion are shown.

Inhibition Studies of 2'-O-(R-2-amino-3-methoxypropyl) AONs Against miR-21

The instant synthesized serinyl functionalized 2'-O-(R-2-amino-3-methoxypropyl) (2'-O-R-AMP) modified uridine at 3 positions i.e. 2'-O-[R-(2-amino-3-methoxy)propyl uridine phosphoramidite ($U^{R-AMP}$, R-14) was investigated for its inhibitory efficacy against miRNA in a cell culture based system. Owing to the oncogenic nature of miR-21, a model of miRNA was selected.

The antisense potency of 2'-O-[R-(2-amino-3-methoxy) propyl uridine phosphoramidite in the form of 3 $U^{R-AMP}$ monomers at position 2, 8 and 14 and two abasic serinyl cappings at both 5'- and 3'-end to enhance nuclease resistance, (the sequence is designated as AMO-2 i.e. anti-miR oligonucleotides) is compared with LNA (locked nucleotide sequence) which is antisense to miR-21 having 4 LNA modifications at underlined cytosines indicated in Scheme 5 and fully modified 2'-OMe RNA designated as AMO-1.

SCHEME 5:
Sequence modifications of LNA, AMO-1 and AMO-2 (anti-miR oligonucleotides).

LNA sequence: TCAACATCAGTCTGATAAGCTA
AMO-1 sequence: ucaacaucagucugauaagcua
AMO-2 sequence: SS-$U^{R-AMP}$caaca$U^{R-AMP}$caguc$U^{R-AMP}$gauaagcua-SS Where C = 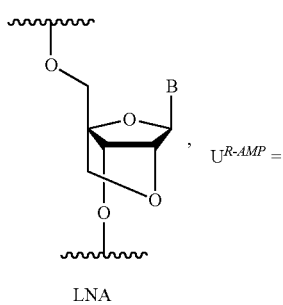 , $U^{R-AMP}$ = 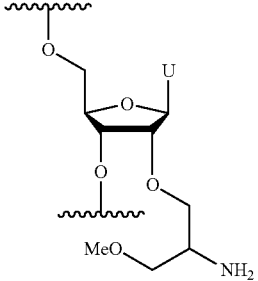 and S = 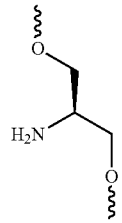

LNA

To preserve the duplex stability with target RNA and to enhance the stabilty against nucleases To enhance the stability against nucleases In sequences, all uppercase letters denote deoxyribonucleotides and lower case letters denote 2'-O-methyl-ribonucleotides. All linkages are phosphodiesters.

i) Effect on miR-21 Levels

The antisense potency of ODN containing LNA modifications (LNA sequence), 2'-OMe RNA (AMO-1) and serinyl derivatized 2'-OMe RNA (AMO-2) having modifications was compared, thus the functional potency of all three AMOs against miR-21 was determined by a dual luciferase screen. The reporter plasmid (pEZX-MT01, Genecopoeia) expresses firefly gene fused with the 3'UTR of PDCD4 which is a one of the established bonafide target of miR-21 target and a *renilla* gene for normalization of signal accounting for variability in transfection.

Figure 4:
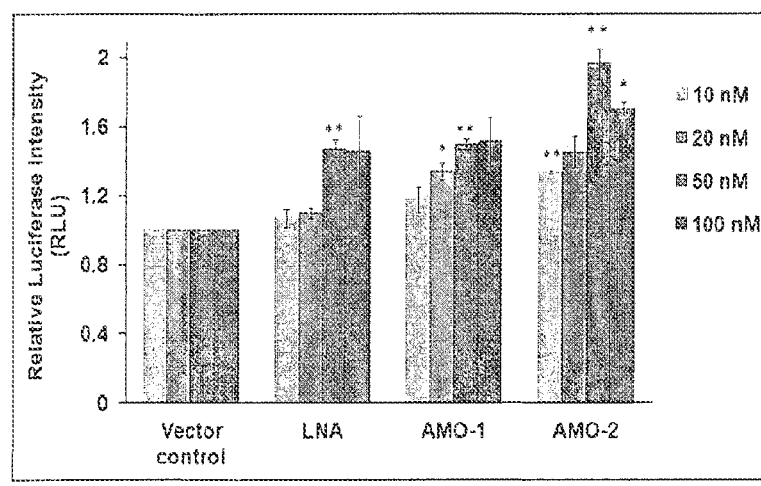
FIG. 4 depicts comparison of the potency of antisense treatments against miRNA-21. Cells transfected with different concentrations (10 to 100 nM) of LNA, AMO-1 and AMO-2 for 24 hrs were analyzed for luciferase intensity. Concentration dependent increase in luciferase intensity is observed for different oligonucleotides with the intensity getting saturated at 100 nM. AMO-2 shows a ~2 fold increase in luciferase luminescence at 50 nM as compared to LNA and AMO-1. (LNA: Locked Nucleic acid, AMO: Anti-miRNA oligonucleotides).

The reporter construct was co-transfected with the AMOs at four concentrations (10 to 100 nM) and post 24 hrs were assayed for *renilla* and firefly luciferase intensity. Transfection of the oligonucleotides resulted in antagonism of miRNA-21, as shown by specific increase in levels of the relative luciferase intensity. (FIG. 4)

Among the three oligonucleotides, AMO-2 was found to be most potent with a ~2 fold increment of luciferase intensity at 50 nM concentration with respect to LNA oligonucleotide that has been shown to be potent inhibitor for miRNA-21. Saturation of the luminescence was observed at 100 nM for all the three AMOs, AMO-1 and AMO-2 were found to be functionally potent at 50 nM, thus affirming this concentration for further experiments.

ii) Identification of Mechanism of Inhibition of miRNA-21 by AMO

Multiple mechanisms of mi-RNA inhibition by the AMO's include steric blocking, miRNA degradation or miRNA sequestration. In order to assess the mechanism by which AMO-1 and AMO-2 act, the levels of mature miRNA post transfection with the respective AMOs were determined (FIG. 5). Significant repression of mature miRNA-21 levels to ~60% and ~80% after transfection with AMO-1 and AMO-2 respectively for 24 hrs was determined. AMO-2 was found to efficaciously repress miRNA-21 levels more than AMO-1 which might be due to its serinyl capping at 3' and 5' ends rendering it less susceptible to exonucleases. Also, since the mature miRNA levels are decreased, it excludes the possibility of steric blocking. Nevertheless, other possibility would be that these AMOs might act via recruiting RNAse H or other enzymes thus causing degradation of miR-21.

iii) Western Blot Analysis to Determine Translation Repression

Translational repression is considered as a major mechanism for miRNA regulation of target gene expression. The extent of suppression of miR-21 targets such as PDCD4 (Programmed cell death 4) and PTEN (Phosphatase and tensin homolog) target levels by AMOs, was examined by Western blot (FIG. 6). It was shown that the PDCD4 and PTEN levels increased after transfection with AMOs. The highest increase was for AMO-2, which further confirms it is more potent than AMO-1.

Western blot analysis shows an inverse correlation of miR-21 targets PTEN and PDCD4 in response to AMOs. The most potent AMO was AMO-2. LNA was taken as positive control and GAPDH (Glyceraldehyde 3-phosphate dehydrogenase) as the loading control. Data shown is the mean±SEM of three independent experiments. *p-value<0.05, **p-value<0.001 indicates significant statistical difference between the oligonucleotide treated and untreated control.

iv) Effect of AMO's on Proliferation of Cancer Cells miR-21 is known to promote migration and proliferation in cancer cells. The capacity of cancer cells to metastasize as a result of the knock down of miR-21 was determined (FIG. 7).

Two different cell lines differing in their properties to metastasize, MCF-7 and MDA-MB-231 were selected. AMO-1 and AMO-2 were transfected and a wound repair assay was performed (FIG. 7). After 24 hrs, the cells treated with AMOs had delayed migrating as compared to the untransfected cells. Knockdown of miR-21 suppressed migration by ~30 fold in case of AMO-1 and ~40 fold in case of AMO-2 in MCF-7 cells. In MDA-MB-231, the suppression was ~20 fold in AMO-1 and ~30 fold in AMO-2.

miR-21 is known to promote proliferation and migration in tumor cells. Knockdown of miR-21 by LNA/AMO-1/AMO-2 suppresses the migration capacity as compared to the untreated control. Wound repair in case of AMO-1 and AMO-2 at 50 nM is inhibited as compared to untreated control. LNA is taken as a positive control.

v) Cytotoxicity Studies

Another important feature of chemically modified oligonucleotides for their use for therapeutic intervention is the issue of cytotoxicity. To examine this, concentration dependent cell viability assay from 10 nM to 100 nM was performed. There was no measurable cytotoxicity upto 100 nM for both AMO-1 and AMO-2 making it suitable candidates for the development potent therapeutic in future. (FIG. 8)

Cells were transfected with different concentrations (10 to 100 nM) of LNA, AMO-1 and AMO-2 for 24 hrs. Cell viability was measured by MTT assay as compared to the untreated control. The viability of the cells remains unaffected upto 100 nM of the three oligonucleotides thus exhibiting no measurable cytotoxicity. Data shown is the mean±SEM of three independent experiments.

ADVANTAGES OF PRESENT INVENTION

The inventors have thus transformed MOE modification into a synergy of chirality, positive charge and hydration module, all in one, in the modified AONs. The amino pendant groups have additional advantages also in improved kinetics of binding and efficient cellular uptake. The potent inhibition of miR-21 is achieved by chemically modified 2'-OMe RNA oligonucleotide. The serinyl capping at 3'- and 5'-ends along with three UR-AMP monomers enhances the nuclease resistance and efficacy of 2'-OMe RNA.

EXAMPLES

The following examples are given by way of illustrating the present invention and should not be construed to limit the scope of the invention

Example 1

(R)-benzyl (1-hydroxy-3-methoxypropan-2-yl)carbamate, R-2

N-Cbz protected-L-serine-methyl ester 1 (39.5 mmol, 10 g) was dissolved in dry acetonitrile (250 mL), followed by the addition of $Ag_2O$ (98.8 mmol, 22.8 g) and MeI (197.5 mmol, 12.7 mL) and the reaction mixture was vigorously stirred at room temperature for 12 hours. Reaction mixture was filtered and the filtrate was concentrated under reduced pressure to give the O-methylated compound. The crude colourless residue was dissolved in MeOH (500 mL) and $NaBH_4$ (150 mmol, 5.6 g) was added fraction wise at 0° C. for a period of 1 hour and the mixture was kept for stirring at room temperature for another 6-8 hours. Excess $NaBH_4$ was quenched with saturated $NH_4Cl$ solution, followed by the removal of MeOH under reduced pressure. The crude reaction mixture was extracted with ethyl acetate. The organic extract was washed with brine solution and dried over anhydrous sodium sulphate. Ethyl acetate was removed under reduced pressure to give the crude product and was purified through column chromatography (eluted in 20% ethyl acetate in petroleum ether) to yield R-2 as a colourless liquid in 83% (7.8 g) over two steps. $^1$H NMR (CDCl$_3$, 200 MHz): δ 2.53 (bs, 1H), 3.35 (s, 3H), 3.55-3.86 (m, 5H), 5.11 (s, 2H), 5.43 (bs, 1H), 7.36-7.37 (m, 5H). $^{13}$C NMR (CDCl$_3$, 100 MHz): δ 51.8, 58.7, 62.1, 66.4, 71.7, 127.7, 128.1, 136.0, 156.2. HRMS (EI) Mass calcd for C12H18O4N (M+H) 240.1230, found 240.1229.

Example 2

(S)-benzyl (1-methoxy-3-((trimethylsilyl)oxy)propan-2-yl)carbamate, S-3

To a stirred solution of R-2 (16.7 mmol, 4 g) and NEt$_3$ (83.5 mmol, 11.7 mL) in dry acetonitrile (70 mL), TMS-Cl (25.1 mmol, 3.1 mL) was added and stirring was continued for another 1 hour. The reaction mixture was diluted with ethyl acetate. Water wash and brine wash were given to the organic layer. The organic layer was dried over anhydrous sodium sulphate, solvents removed in vacuo and the crude compound was purified through column chromatography (eluted in 5% ethyl acetate in petroleum ether) to give S-3 as a colourless liquid in 83% yield (4.3 g). $^1$H NMR (CDCl$_3$, 200 MHz): δ 0.10 (s, 9H), 3.32 (s, 3H), 3.35-3.39 (m, 1H), 3.47-3.50 (m, 1H), 3.56-3.60 (m, 1H), 3.68-3.73 (m, 1H), 3.84 (m, 1H), 5.09 (s, 2H), 5.27 (bs, 1H), 7.29-7.34 (m, 5H). $^{13}$C NMR (CDCl$_3$, 100 MHz): δ 0.8, 51.3, 58.6, 60.6, 66.4, 70.3, 127.8, 128.2, 136.3, 155.7. HRMS (EI) Mass calcd for C15H26O4NSi (M+H) 312.1626, found 312.1622.

Example 3

(R)-benzyl (1-((tert-butyldimethylsilyl)oxy)-3-hydroxypropan-2-yl)carbamate, R-4

N-Cbz protected-L-serine-methyl ester 1 (39.5 mmol, 10 g) was dissolved in dry DCM (200 mL), followed by the addition of imidazole (98.8 mmol, 6.7 g) and TBS-Cl (47.4 mmol, 7.1 g). The reaction mixture was diluted with DCM and the DCM layer was washed with water and brine solution. Organic layer was dried over anhydrous sodium sulphate and solvent removed in vacuo to result the crude TBS protected ester, which was directly subjected to NaBH$_4$ reduction. The colourless residue was dissolved in methanol (500 ml) and NaBH$_4$ (150 mmol, 5.6 g) was added fraction wise at 0° C. for a period of 1 hour and then continued stirring at room temperature for another 6 hours. Excess NaBH$_4$ was quenched with saturated NH$_4$Cl solution, followed by the removal of MeOH under reduced pressure and the crude compound was extracted with ethyl acetate. The organic extract was washed with brine and dried over anhydrous sodium sulphate. Ethyl acetate was removed under reduced pressure to give the crude product and was purified through column chromatography (eluted in 15% ethyl acetate in petroleum ether) to yield R-4 as a colourless liquid in 87% (11.6 g) over two steps. $^1$H NMR (CDCl$_3$, 200 MHz): δ 0.05 (s, 6H), 0.88 (s, 9H), 2.64 (bs, 1H), 3.66-3.84 (m, 5H), 5.11 (s, 2H), 5.38-5.41 (m, 1H), 7.35-7.38 (m, 5H). $^{13}$C NMR (CDCl$_3$, 50 MHz): δ −5.6, 18.1, 25.7, 53.0, 63.0, 63.4, 66.7, 128.0, 128.4, 136.2, 158.2. HRMS (EI) Mass calcd for C17H30O4NSi (M+H) 340.1939, found 340.1945.

Example 4

(R)-benzyl (1-((tert-butyldimethylsilyl)oxy)-3-methoxypropan-2-yl)carbamate, R-5

To a stirred solution of R-4 (29.4 mmol, 10 g) and MeI (147.4 mmol, 9.5 mL), Ag$_2$O (73.5 mmol, 16.9 g) was added and the reaction mixture was vigorously stirred at room temperature for 12 hours. Reaction mixture was filtered and the filtrate was concentrated under reduced pressure. Crude compound was purified through column chromatography (eluted in 5% EtOAc in petroleum ether) to result R-5 as a colourless liquid in 91% (9.4 g) yield. $^1$H NMR (CDCl$_3$, 200 MHz): δ 0.05 (s, 6H), 0.88 (s, 9H), 3.33 (s, 3H), 3.37-3.77 (m, 4H), 3.78-3.86 (m, 1H), 5.10 (s, 2H), 7.35-7.38 (m, 5H). $^{13}$C NMR (CDCl$_3$, 100 MHz): δ −5.6, 18.1, 25.7, 51.5, 58.8, 61.3, 66.6, 70.4, 128.0, 128.4, 136.4, 155.9. HRMS (EI) Mass calcd for C18H32O4NSi (M+H) 354.2095, found 354.2089.

Example 5

A General Procedure for Synthesis of 2′-O-functionalization of 2,2′-anhydrouridine: S-7/R-8

Desiccated 2,2′-anhydrouridine 6 (6.6 mmol, 1.5 g) was dissolved in dry DMA (10 mL) followed by the addition of BF$_3$.OEt$_2$ (10 mmol, 1.2 mL) under argon atmosphere. After 2 minutes, the activated/protected silyl ethers S-3/R-5 (13.2 mmol) were added and stirred at 130° C. for 8 h-12 h. DMA was removed partially in vacuo, followed by the dilution with MeOH and the reaction mixture was column purified (eluted in 5% MeOH in DCM) to result S-7/R-8 as a white solid in 60-68% yield. 5-7 $^1$H NMR (DMSO-d6, 200 MHz): δ 3.21 (s, 3H), 3.49-3.63 (m, 5H), 3.82-3.9 (m, 3H), 4.03-4.10 (m, 1H), 5.01-5.05 (m, 3H), 5.14 (t, 1H, J=4.69, 9.75 Hz), 5.60-5.65 (m, 1H), 5.79 (d, 1H, J=4.15 Hz), 7.35 (m, 5H), 7.92 (d, 1H, J=7.76 Hz). $^{13}$C NMR (DMSO-d6, 200 MHz): δ 50.0, 58.1, 59.9, 65.3, 68.1, 69.1, 70.9, 81.5, 84.4, 86.1, 101.6, 12.7.7, 128.3, 136.9, 140.3, 150.3, 155.8, 163.1. HRMS (EI) Mass calcd for C21H27O9N3Na (M+Na) 488.1640, found 488.1630. R-8 $^1$H NMR (DMSO-d6, 400 MHz): δ 3.22 (s, 3H), 3.51-3.68 (m, 5H), 3.78-3.93 (m, 3H), 4.09-4.13 (m, 1H), 4.97-5.051 (m, 3H), 5.16 (t, 1H, J=4.77, 9.54 Hz), 5.64-5.66 (m, 1H), 5.84 (d, 1H, J=4.77 Hz), 7.36 (m, 5H), 7.92 (d, 1H, J=8.03 Hz). $^{13}$C NMR (DMSO-d6, 100 MHz): δ 50.3, 58.4, 60.6, 65.5, 68.6, 69.3, 71.4, 81.8, 85.0, 86.3, 102.0, 128.0, 128.0, 128.5, 137.2, 140.6, 150.7, 156.0, 163.4 HRMS (EI) Mass calcd for C21H28O9N3 (M+H) 466.1820, found 466.1822.

Example 6

5′-O-DMT Protection of 2′-O-Functionalized Uridine (S-9/R-10)

2′-O-functionalized uridine S-7/R-8 (3.44 mmol, 1.6 g) was dissolved in dry pyridine (10 mL) and DMT-Cl (3.61 mmol, 1.22 g) and catalytic amount of DMAP (~20 mg) were added. Reaction mixture was kept for stirring at room temperature for 5-6 hours. Pyridine was removed under reduced pressure and the residue was diluted with ethyl acetate. 10% aqueous NaHCO$_3$, water and brine solution wash were given to the organic layer. The organic layer was dried over anhydrous Na$_2$SO$_4$ and concentrated to dryness. Crude compound was column purified (eluted in 70% ethyl acetate in petroleum ether) to result S-9/R-10 as a white foam in 89% yield, S-9 $^1$H NMR (CDCl$_3$, 200 MHz): δ 3.33 (s, 3H), 3.42-3.54 (m, 5H), 3.8 (s, 6H), 3.91-4.04 (m, 4H), 4.44 (bs, 1H), 5.09 (s, 2H), 5.23 (d, 1H, J=8.21 Hz), 5.32 (d, 1H, J=7.96 Hz), 5.89 (s, 1H), 6.83-6.87 (m, 4H), 7.31-7.40 (m, 14H), 8.02 (d, 1H, J=8.08 Hz), 8.26 (bs, 1H). $^{13}$C NMR (CDCl$_3$, 125 MHz): δ 50.1, 55.0, 58.9, 61.0, 66.6, 68.2, 70.9, 71.4, 82.8, 82.9, 86.8, 87.5, 101.8, 113.1, 126.9, 127.8, 128.0, 128.3, 129.9, 130.0, 134.9, 135.2, 136.2, 139.9, 144.2, 150.2, 156.6, 158.4, 158.5, 163.8. HRMS (EI) Mass calcd for C42H45O11Na (M+Na) 790.2946, found 790.2931. R-10 $^1$H NMR (CDCl$_3$, 400 MHz): δ 3.31 (s, 3H), 3.50-3.52 (m, 5H), 3.76 (m, 6H), 3.90-3.91 (m, 1H), 4.02-4.04 (m, 3H), 4.39-4.42 (m, 1H), 5.07-5.08 (m, 2H), 5.27 (d, 1H, J=8.24 Hz), 5.64 (d, 1H, J=8.24 Hz), 5.92 (d, 1H, J=0.92 Hz), 6.82-6.84 (m, 4H), 7.27-7.39 (m, 14H), 7.96 (d, 1H, J=8.24 Hz). $^{13}$C NMR (DMSO-d6, 100 MHz): δ 50.2, 55.0, 58.9, 61.2, 66.7, 68.3, 70.9, 71.5, 83.1, 83.2, 86.8, 87.2, 101.9, 113.1, 127.0, 127.8, 12.8.0, 128.3, 129.9, 130.0, 134.9, 135.3, 136.1, 139.8, 144.2, 150.3, 156.2, 158.50, 158.54, 163.7. HRMS (EI) Mass calcd for C42H45O11N3Na (M+Na) 790.2946, found 790.2946.

Example 7

Change of Amine-Protecting Group at the 2-tether: (S-11/R-12)

The 5'-O-DMT protected 2'-O-functionalized uridine derivative S-9/R-10 (2.3 mmol, 1.8 g) was dissolved in MeOH (10 mL) followed by the addition of 10% Pd—C (10% w/w, 0.18 g). Then reaction mixture was subjected to catalytic hydrogenation at 65 psi of hydrogen pressure for 6 h. After the TLC analysis, reaction mixture was filtered over celite and the removal of methanol in vacuo gave free amine. Without further purification amine was subjected to trifluoroacetyl protection. To the crude amine (2.2 mmol, 1.4 g) dissolved in MeOH (15 mL), NEt$_3$ (3.3 mmol, 0.46 mL) was added. Ethyltrifluoroacetate was added to reaction mixture and the mixture was kept for stirring at room temperature for 8-10 h. MeOH was removed on rota evaporator and the reaction mixture was diluted with ethylacetate. The organic layer was washed with water and 5% aq. NaHCO3 and the organic layer was dried over anhydrous Na$_2$SO$_4$, concentrated in vacuo. Crude compound was column purified to furnish S-11/R-12 as white foam in 86-88% yield (eluted in 55% ethylacetate in petether). S-11 $^1$H NMR (CDCl$_3$, 500 MHz): δ 3.40 (s, 3H), 3.52-3.63 (m, 5H), 3.81 (s, 6H), 3.82-3.85 (m, 1H), 3.93 (dd, 1H, J=1.8 and 4.9 Hz), 4.03-4.06 (m, 1H), 4.09 (dd, 1H, J=4.8 and 10.0 Hz), 4.33-4.37 (m, 1H), 4.42-4.46 (m, 1H), 5.30 (dd, 1H, J=5.6=2.1 and 8.24 Hz), 5.92 (d, 1H, J=1.5 Hz), 6.85-6.86 (m, 4H), 7.25-7.39 (m, 9H), 8.00 (d, 1H, J5,6=8.24 Hz). $^{13}$C NMR (CDCl$_3$, 500 MHz): δ 49.43, 55.2, 59.3, 61.2, 68.5, 70.1, 70.6, 83.4, 83.6, 87.1, 87.5, 102.3, 113.2, 113.3, 127.2, 128.0, 128.1, 130.0, 130.1, 135.0, 135.2, 139.7, 144.2, 150.2, 158.7, 162.7. HRMS (EI) Mass calcd for C36H38O10N3F3Na (M+Na) 752.2402, found 752.2391. R-12 $^1$H NMR (DMSO-d6, 400 MHz): δ 3.24 (s, 3H), 3.43-3.45 (m, 3H), 3.64-3.68 (m, 2H), 3.74 (s, 6H), 3.83 (m, 1H), 3.94-3.99 (m, 3H), 4.16-4.19 (m, 3H), 5.17 (d, 1H, J=7.50 Hz), 5.27 (dd, 1H, J5,6=2.0 and 8.17 Hz), 5.77 (d, 1H, J=2.75 Hz), 6.89-6.91 (m, 4H), 7.24-7.39 (m, 9H), 7.70 (d, 1H, J5,6=8.19 Hz). $^{13}$C NMR (CDCl$_3$, 500 MHz): δ 49.44, 55.2, 59.2, 60.9, 68.4, 69.3, 70.4, 83.1, 83.4, 87.1, 87.8, 102.2, 113.1, 113.3, 127.0, 128.0, 128.1, 130.0, 131.0, 135.0, 135.2, 139.7, 144.3, 150.3, 158.6, 158.7. HRMS (EI) Mass calcd for C36H38O10N3F3Na (M+Na) 752.2402, found 752.2405.

Example 8

A General Procedure for the Synthesis of Phospharamidite Derivatives (S-13/R-14):

To the compound S-11/R-12 (0.68 mmol, 500 mg) dissolved in dry DCM (10 mL), DIPEA (1.7 mmol, 0.29 mL) was added. 2-cyanoethyl-N,N,-diisopropyl-chloro phosphine (0.81 mmol, 0.18 mL) was added to the reaction mixture at 0° C. and continued stirring at room temperature for 3 hours. The contents were diluted with DCM and washed with 5% NaHCO$_3$ solution. The organic phase was dried over anhydrous sodium sulphate and concentrated to white foam. The residue was re-dissolved in DCM and the compound was precipitated with n-hexane to obtain corresponding phospharamidite derivatives in 88-92% yield.

Phosphoramidite S-13: $^{31}$P NMR (Acetonitrile, D$_2$O as external standard, 400 MHz): δ 149.22, 149.68. HRMS (EI) Mass calcd for C45H55O11N5F3PNa (M+Na) 952.3480, found 952.3516. Phosphoramidite R-14: $^{31}$P NMR (Acetonitrile, D$_2$O as external standard, 400 MHz): δ 149.52, 150.62. HRMS (EI) Mass calcd for C45H56O11N5F3P (M+H) 930.3661, found 930.3674. S-S amidite 1b: $^{31}$P NMR (Acetonitrile, D$_2$O as external standard, 161.8 MHz): δ 149.17, 149.20 HRMS (EI) Mass calcd for C$_{35}$H$_{43}$O$_6$N$_3$F$_3$PNa (M+Na) 712.2734, found 712.2728.

SVPD digestion: Stability of the oligonucleotides Seq. 22-31 towards exo-nucleases SVPD (snake venom phosphodiesterase) was analyzed by RP-HPLC. 7.5 µM of oligonucleotide in 300 µL of Tris-HCl buffer (pH=7.5, 10 mM Tirs-HCl, 8 mM MgCl2) were incubated at 37° C. for 15 minutes. SVPD 5 ng/µL was added to the oligonucleotide incubated at 37° C. and aliquots of 20 µL were removed at time intervals of 0, 2, 5, 10, 20, 30, 60, 90, 120, 150, 180, 210 and 240 minutes. Aliquots were kept at 90° C. for 2 minutes prior to their analysis on RP-HPLC with an increasing gradient (A: 5% acetonitrile and B: 30% acetonitrile in 0.1N triethylammonium acetate, pH 7.0). And the % of the intact oligonucleotides (based on the % area of the peaks) was plotted against the time intervals.

The invention claimed is:

1. A chiral serinyl functionalized tethered oligonucleotide having Formula I,

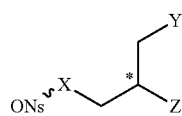

Formula I wherein
X is O or S;
Y is OR, wherein R is ($C_{1-10}$) alkyl, heteroaryl, aryl, or alkyl aryl;
Z is $NH_2$, $NHR^1$, $NH(R^1)_2$, guanidine or NHP, wherein $R^1$ is H, ($C_{1-10}$) alkyl, heteroaryl, aryl, or alkyl aryl, and P is a protecting group selected from Cbz, TFA, DMT, TBS, and TMS; and
ONs is an oligonucleotide.

2. The chiral serinyl functionalized tethered oligonucleotide as claimed in claim 1, wherein X is O.

3. The chiral serinyl functionalized tethered oligonucleotide as claimed in claim 1, wherein Z is $NHR^1$, further wherein $R^1$ is H, ($C_{1-10}$) alkyl, heteroaryl, aryl, or alkyl aryl.

4. The chiral serinyl functionalized tethered oligonucleotide as claimed in claim 1, wherein X is O; Y is OMe; and Z is $NH_2$.

5. The chiral serinyl functionalized tethered oligonucleotide as claimed in claim 1, wherein the chirality of tether in oligonucleotides is either R or S.

6. The chiral serinyl functionalized tethered oligonucleotide as claimed in claim 1, wherein the oligonucleotide is a DNA or an RNA.

7. The chiral serinyl functionalized tethered oligonucleotide according to claim 1, wherein the chiral serinyl functionalized oligonucleotide is obtained from a 2'-O-functionalization of a nucleoside unit with R-(2-amino-3-methoxy) propyl and S-(2-amino-3-methoxy)propyl and incorporation into the ONs.

8. The chiral serinyl functionalized tethered oligonucleotide according to claim 7, wherein a 2' position of a ribose sugar unit in at least two nucleic acid units are functionalized with R-(2-amino-3-methoxy)propyl or S-(2-amino-3-methoxy)propyl, and the at least two nucleic acid units functionalized with R-(2-amino-3-methoxy)propyl or S-(2-amino-3-methoxy)propyl are introduced in the oligonucleotide sequence either continuously or evenly dispersed throughout the sequence.

9. The chiral serinyl functionalized tethered oligonucleotide according to claim 7, wherein a chiral serinyl functionalized phospharamidite is introduced at either a 3'- or 5'-end of a nucleotide sequence with R/S serinyl derivative, (S)-unit.

10. The chiral serinyl functionalized tethered oligonucleotide according to claim 8, wherein the modified nucleoside containing the R/S serinyl derivative at 2' of the sugar unit is introduced at specific positions in a nucleotide sequence selected from 3', 5' and central region.

11. A process for preparing the chiral serinyl functionalized tethered oligonucleotide of formula I as claimed in claim 1, comprising the steps of:
a) preparing a basic serinyl amidite (S); and,
b) introducing the basic serinyl amidite (S) to the oligonucleotide with S-S-amidite at 3'- and 5'-positions to obtain 3'- and 5'-protected R/S chiral serinyl functionalized tethered oligonucleotides.

12. The process for preparing an (S)-serinyl functionalized tethered oligonucleotide of formula I as claimed in claim 11, the process for preparing comprising the steps of as depicted in scheme below;
a) protecting a hydroxyl group of the serine ester (1) to obtain DMT-ether using dimethoxytrityl chloride, followed by ester reduction to alcohol to furnish (1a) followed by changing the amino protecting group of (1a) from —NH-Cbz to —NH-TFA using ethyltrifluoro acetate and subsequent phosphitylation to obtain the S amidite (1b);

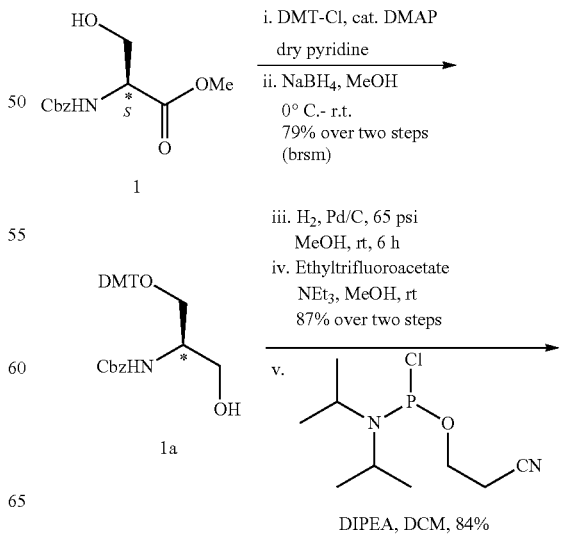

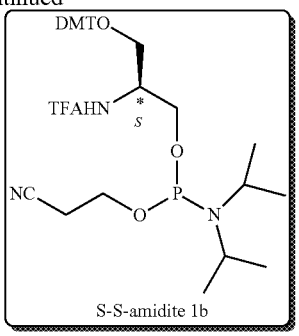

and b) introducing the S amidite (1b) to the oligonucleotide at 3'- and 5'-positions to obtain (S)-serinyl functionalized tethered oligonucleotides.

13. A process for preparing the chiral serinyl functionalized tethered oligonucleotide of formula I as claimed in claim 1, the process for preparing comprising the steps of:

a) stereospecifically synthesizing enantiomeric serinyl derivatives [R/S-(2-amino-3-methoxy) propanol tethers (R-AMP and S-AMP) from the natural amino acid L-serine;

b) 3'-O-phosphitylation of 2'-O-[R/S-(2-amino-3-methoxypropyl)]nucleosides to obtain the 3'-O-phosphoramidite derivatives of 2'-O-R-AMP and 2'-O-S-AMP units; and c) Introducing a basic serinyl(S) capping to the oligonucleotide with R/S-S-amidite at 3'- and 5'-positions to obtain R/S chiral serinyl functionalized tethered oligonucleotides.

14. The process of preparing the chiral serinyl functionalized tethered oligonucleotides of formula I as claimed in claim 13, wherein the [R/S-(2-amino-3-methoxy) propanol tethers (R-AMP and S-AMP) are (S)-benzyl (1-methoxy-3-((trimethylsilyl)oxy)propan-2-yl)carbamate (S-3) or (R)-benzyl (1-((tert-butyldimethylsilyl)oxy)-3-methoxypropan-2-yl)carbamate (R-5).

15. The process of preparing the chiral serinyl functionalized tethered oligonucleotides of formula I as claimed in claim 13, wherein the stereospecific synthesis of (S)-benzyl (1-methoxy-3-((trimethylsilyl)oxy)propan-2-yl)carbamate (S-3) comprising:

a) O-methylation of N-Cbz-protected-L-serine methyl ester 1 using silver oxide and methyl iodide followed by reduction to obtain (R)-benzyl (1-hydroxy-3-methoxypropan-2-yl)carbamate (R-2), and b) transforming (R)-benzyl (1-hydroxy-3-methoxypropan-2-yl)carbamate (R-2) into (S)-benzyl (1-methoxy-3-((trimethylsilyl)oxy)propan-2-yl)carbamate (S-3) using trimethylsilylchloride (TMS-Cl).

16. The process of preparing the chiral serinyl functionalized tethered oligonucleotides of formula I as claimed in claim 13, wherein (R)-benzyl (1-((tert-butyldimethylsilyl)oxy)-3-methoxypropan-2-yl)carbamate (R-5) is synthesized by the steps comprising:

a) protecting serine ester 1 with tertiarybutyldimethylsilyl ether followed by reduction to obtain (R)-benzyl (1-((tert-butyl di methyl silyl)oxy)-3-hydroxypropan-2-yl) carbamate (R-4),

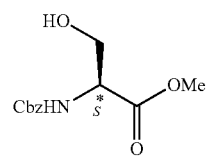

and b) methylating free hydroxyl group in (R)-benzyl (1-((tert-butyldimethylsilyl)oxy)-3-hydroxypropan-2-yl) carbamate (R-4) to give (R)-benzyl (1-((tert-butyldimethylsilyl)oxy)-3-methoxypropan-2-yl)carbamate (R-5).

17. A process for preparing 2'-O-[S/R-(2-amino-3-methoxy)propyl uridine phosphoramidite comprising the steps as depicted in scheme below:

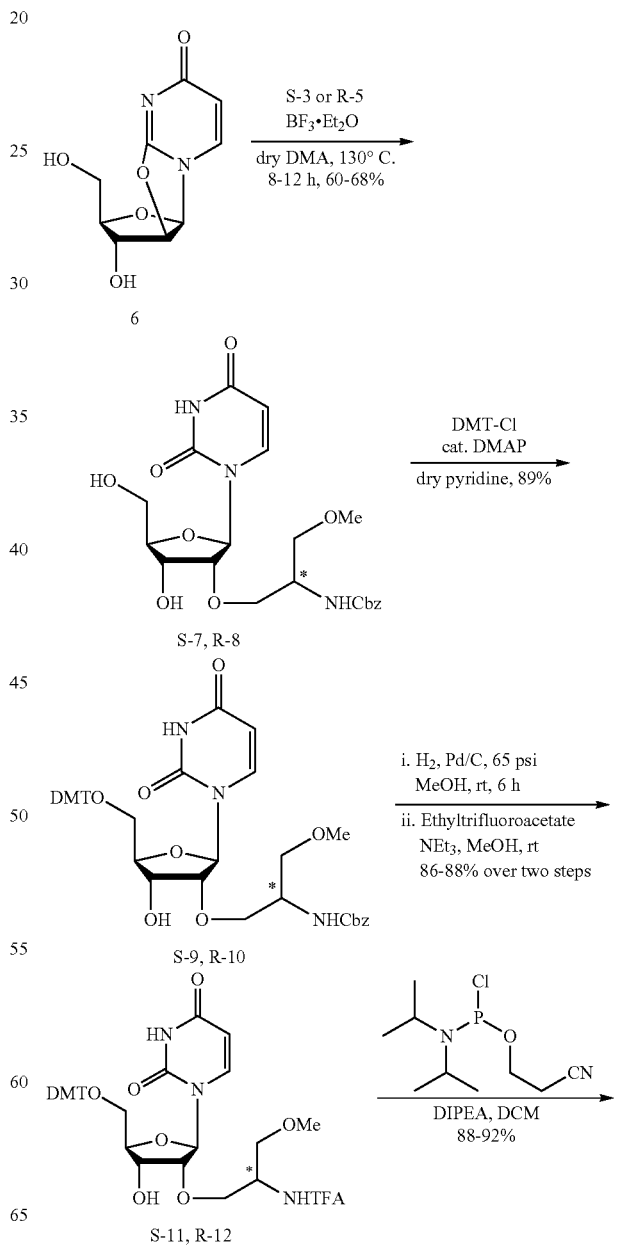

-continued

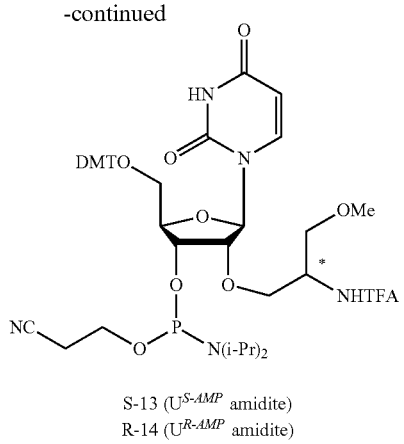

S-13 (U<sup>S-AMP</sup> amidite)
R-14 (U<sup>R-AMP</sup> amidite)

a) reacting 2,2'-anhydrouridine with 2 equivalents of TMS-ethers, (S)-benzyl (1-methoxy-3-((trimethylsilyl)oxy)propan-2-yl)carbamate[S-3] or TBS-silyl ethers, (R)-benzyl (1-((tert-butyldimethylsilyl)oxy)-3-methoxypropan-2-yl)carbamate[R-5] to obtain 2,2'-anhydro ring-opened products S-7 or R-8;

b) protecting 5'-end of S-7 and R-8 compounds as —O-DMT ether to obtain 5'-O-DMT protected 2'-O-functionalized uridine S-9 or R-10 respectively;

c) deprotecting the N-Cbz protecting group of the 2'-O-functionalized uridine S-9 and R-10 by hydrogenation in presence of 10% Pd/C under pressure, followed by protecting the primary amino group to obtain trifluoroacetyl derivatives S-11 and R-12; and d) preparing phosphoramidite derivatives S-13 and R-14 by phosphitylation of S-11 and R-12.

18. The chiral serinyl functionalized tethered oligonucleotide according to claim 9, wherein the modified nucleoside containing the R/S serinyl derivative at 2' of the sugar unit is introduced at specific positions in a nucleotide sequence selected from 3', 5' and central region.

* * * * *